(12) United States Patent
Ganzer et al.

(10) Patent No.: US 10,953,229 B1
(45) Date of Patent: Mar. 23, 2021

(54) THERAPEUTIC WINDOW FOR TREATMENT OF ISCHEMIA BY VAGUS NERVE STIMULATION

(71) Applicant: Battelle Memorial Institute, Columbus, OH (US)

(72) Inventors: Patrick Ganzer, Columbus, OH (US); Seyed Masoud Loeian, Columubs, OH (US); David A Friedenberg, Worthington, OH (US); Doug Weber, Pittsburgh, PA (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 0 days.

(21) Appl. No.: 17/029,192

(22) Filed: Sep. 23, 2020

Related U.S. Application Data

(60) Provisional application No. 62/905,041, filed on Sep. 24, 2019, provisional application No. 62/905,734, filed on Sep. 25, 2019.

(51) Int. Cl.
*A61N 1/36* (2006.01)
(52) U.S. Cl.
CPC ...... *A61N 1/36114* (2013.01); *A61N 1/36139* (2013.01)
(58) Field of Classification Search
None
See application file for complete search history.

(56) References Cited

U.S. PATENT DOCUMENTS

| | | | |
|---|---|---|---|
| 2011/0125041 A1* | 5/2011 | Fischell | A61B 5/0456 600/515 |
| 2012/0010515 A1 | 1/2012 | Zhou et al. | |
| 2012/0185020 A1 | 7/2012 | Simon et al. | |
| 2017/0151433 A1* | 6/2017 | Simon | A61N 2/006 |
| 2018/0146863 A1* | 5/2018 | Libbus | A61B 5/0402 |

FOREIGN PATENT DOCUMENTS

WO 2015138981 A1 9/2015

OTHER PUBLICATIONS

Capilupi, et al.; Vagus Nerve Stimulation and the Cardiovascular System; Cold Spring Harbor Perspectives in Medicine, May 20, 2019, Downloaded from http://perspectivesinmedicine.cshlp.org/ Jul. 17, 2019.
Del Rio, et al.; Effects of acute vagal nerve stimulation on the early passive electrical changes induced by myocardial ischaemia in dogs: heart rate-mediated attenuation, Experimental Physiology; Exp Physiol pp. 931-944, vol. 93.8, Mar. 30, 2008.

(Continued)

*Primary Examiner* — Ankit D Tejani
(74) *Attorney, Agent, or Firm* — Pearne & Gordon LLP

(57) ABSTRACT

Closed-loop stimulation of the Vagus nerve in response to a detected myocardial ischemia state within a therapeutic window can mitigate or reverse effects of the ischemia. This window is between 0 and 50 seconds of the onset of ischemia, before the myocardial ischemia reaches a statistically significant evolution level. A properly trained machine learning system such as a long short-term memory system can be used to analyze cardiovascular features and detect myocardial ischemia within the therapeutic window.

14 Claims, 6 Drawing Sheets

(56) References Cited

OTHER PUBLICATIONS

Vanoli, et al.; Vagal Stimulation and Prevention of Sudden Death in Conscious Dogs With a Healed Myocardial Infarction; Circulation Research, May 1991, pp. 1471-1481, vol. 68, No. 5.

Vimercati, et al.; Acute vagal stimulation attenuates cardiac metabolic response to β-adrenergic stress, Journal of Physiology, 2012, pp. 6065-6074, vol. 590.23.

Goto, et al.; Artificial intelligence to predict needs for urgent revascularization from 12-leads electrocardiography in emergency patients, PLoS One. Jan. 9, 2019. vol. 14, No. 1, pp. 1-10.

Lyon, et al.; Computational techniques for ECG analysis and interpretation in light of their contribution to medical advances. The Royal Society Publishing, 2018, vol. 15, pp. 1-18.

The International Search Report and Written Opinion issued in corresponding International Patent Application No. PCT/US2020/52117; dated Dec. 18, 2020.

* cited by examiner

THERAPEUTIC WINDOW FOR TREATMENT OF ISCHEMIA BY VAGUS NERVE STIMULATION

CROSS REFERENCE TO RELATED APPLICATIONS

This application claims priority to U.S. Provisional Application Ser. No. 62/905,041, filed on Sep. 24, 2019 and entitled "THERAPEUTIC WINDOW FOR TREATMENT OF ISCHEMIA BY VAGUS NERVE STIMULATION", and to U.S. Provisional Application Ser. No. 62/905,734, filed on Sep. 25, 2019 and entitled "THERAPEUTIC WINDOW FOR TREATMENT OF ISCHEMIA BY VAGUS NERVE STIMULATION", the entireties of which are incorporated herein by reference.

BACKGROUND

Myocardial ischemia is a physiological state in which blood flow to the heart is reduced, thereby reducing the oxygen received by the heart. This can lead to irreversible heart damage and/or a heart attack if not treated. Several options currently exist for treating myocardial ischemia. For example, pharmacological drugs can be used to dilate coronary arteries; however, these are often accompanied by debilitating side effects and cannot easily be given during a spontaneous myocardial ischemia episode. Additionally, surgery may be used to graft new blood vessels into the ischemic myocardium for enhanced oxygen delivery; however, open-heart procedures can be extremely dangerous and expensive.

BRIEF SUMMARY

According to a first example of the present disclosure, a stimulation system comprises: at least one sensor configured to monitor physiological data of a subject; a trained machine learning system configured to identify a myocardial ischemia state of the subject based on the monitored physiological data; and an electrode configured to stimulate the Vagus nerve of the subject when the machine learning system identifies the myocardial ischemia state of the subject, wherein: the machine learning system is trained with segments of physiological data, the segments including a rest state and a myocardial ischemia state, and the myocardial ischemia state is identified in the training segments prior to the myocardial ischemia reaching a statistically significant evolution level.

In various embodiments of the first example, the physiological data includes a lead II electrocardiogram (ECG), intraarterial blood pressure, and/or a photoplethysmogram; a heart rate, QRS interval, RT interval, ST interval, Q wave level, ST segment level, ST segment slope, diastolic pressure, systolic pressure, mean arterial pressure, pulse pressure, and/or breath rate are extracted from the physiological data and input to the trained machine learning system; the segments of physiological data include a heart rate, QRS interval, RT interval, ST interval, Q wave level, ST segment level, ST segment slope, diastolic pressure, systolic pressure, mean arterial pressure, pulse pressure, and/or breath rate information; the trained machine learning system comprises a long short-term memory deep learning layer; the electrode is configured to stimulate the Vagus nerve with a biphasic square wave morphology at 0.5-3 mA and 1-60 Hz, with a 100-400 µs pulse width; and/or the electrode is configured to stimulate the Vagus nerve with a biphasic square wave morphology at 2.5 mA and 30 Hz, with a 0.3 millisecond pulse width.

According to a second example of the present disclosure, a stimulation method comprises: monitoring physiological data of a subject; identifying, with a trained machine learning system, a myocardial ischemia state of the subject based on the monitored physiological data; and stimulating the Vagus nerve of the subject when the machine learning system identifies the myocardial ischemia state of the subject, wherein: the machine learning system is trained with segments of physiological data, the segments including a rest state and a myocardial ischemia state, and the myocardial ischemia state is identified in the segments prior to the myocardial ischemia reaching a statistically significant evolution level.

In various embodiments of the second example, the physiological data includes a lead II electrocardiogram (ECG), intraarterial blood pressure, and/or a photoplethysmogram; the method further comprises: extracting a heart rate, QRS interval, RT interval, ST interval, Q wave level, ST segment level, ST segment slope, diastolic pressure, systolic pressure, mean arterial pressure, pulse pressure, and/or breath rate from the physiological data, and inputting the extracted information to the trained machine learning system; the segments of physiological data include a heart rate, QRS interval, RT interval, ST interval, Q wave level, ST segment level, ST segment slope, diastolic pressure, systolic pressure, mean arterial pressure, pulse pressure, and/or breath rate information; the trained machine learning system comprises a long short-term memory deep learning layer; the Vagus nerve is stimulated with a biphasic square wave morphology at 0.5-3 mA and 1-60 Hz, with a 100-400 µs pulse width; and/or the Vagus nerve is stimulated with a biphasic square wave morphology at 2.5 mA and 30 Hz, with a 0.3 millisecond pulse width.

DETAILED DESCRIPTION OF THE DRAWING

Vagal nerve stimulation (VNS) overcomes the above-described shortcomings in current treatment options for myocardial ischemia. In particular, VNS can open coronary arteries to facilitate oxygen delivery, and can decrease the metabolic rate of the myocardium to mitigate myocardial 'work'/oxygen consumption. Further, VNS can act directly and rapidly within the heart tissue thereby mitigating off-target side effects, and can be triggered with temporal precision during a spontaneous episode of myocardial ischemia. Still further, VNS devices can be implanted via a minimally invasive outpatient procedure.

It has been found that such temporal precision optimizes the therapeutic effects of VNS. For example, the benefits of temporal precision of a VNS intervention has been demonstrated in preclinical studies of paralysis and epilepsy. In particular, myocardial ischemia is a cascade of cardiovascular events that can take several seconds to several minutes to fully develop. These events, when detected, can be used to trigger VNS. Because of the progression of events, treating myocardial ischemia with VNS can be time-sensitive and thus VNS should be applied within a 'therapeutic window.' If VNS is applied outside of the window (e.g., too late), then the efficacy of the treatment may be significantly reduced, or the treatment may fail.

In consideration of the above, the present disclosure relates to timely therapeutic treatments for myocardial ischemia that prevent irreversible progression and resulting physiological damage. More particularly, the disclosure relates to closed-loop stimulation of the Vagus nerve in response to a detected myocardial ischemia state within a therapeutic window.

For purposes of the present disclosure, myocardial ischemia has been experimentally modeled in rats anesthetized with isoflurane, then injected with the pharmacological agents dobutamine and norepinephrine (both injected into the arterial blood supply at an infusion rate of 2-10 μg-kg/min). These agents together progressively induce myocardial ischemia mainly by increasing the demand for myocardial oxygen (e.g., via increasing heart rate, metabolic rate, and ventricular wall stress). These agents further decrease the supply of myocardial oxygen (e.g., via constricting the coronary arteries).

Figure 1:
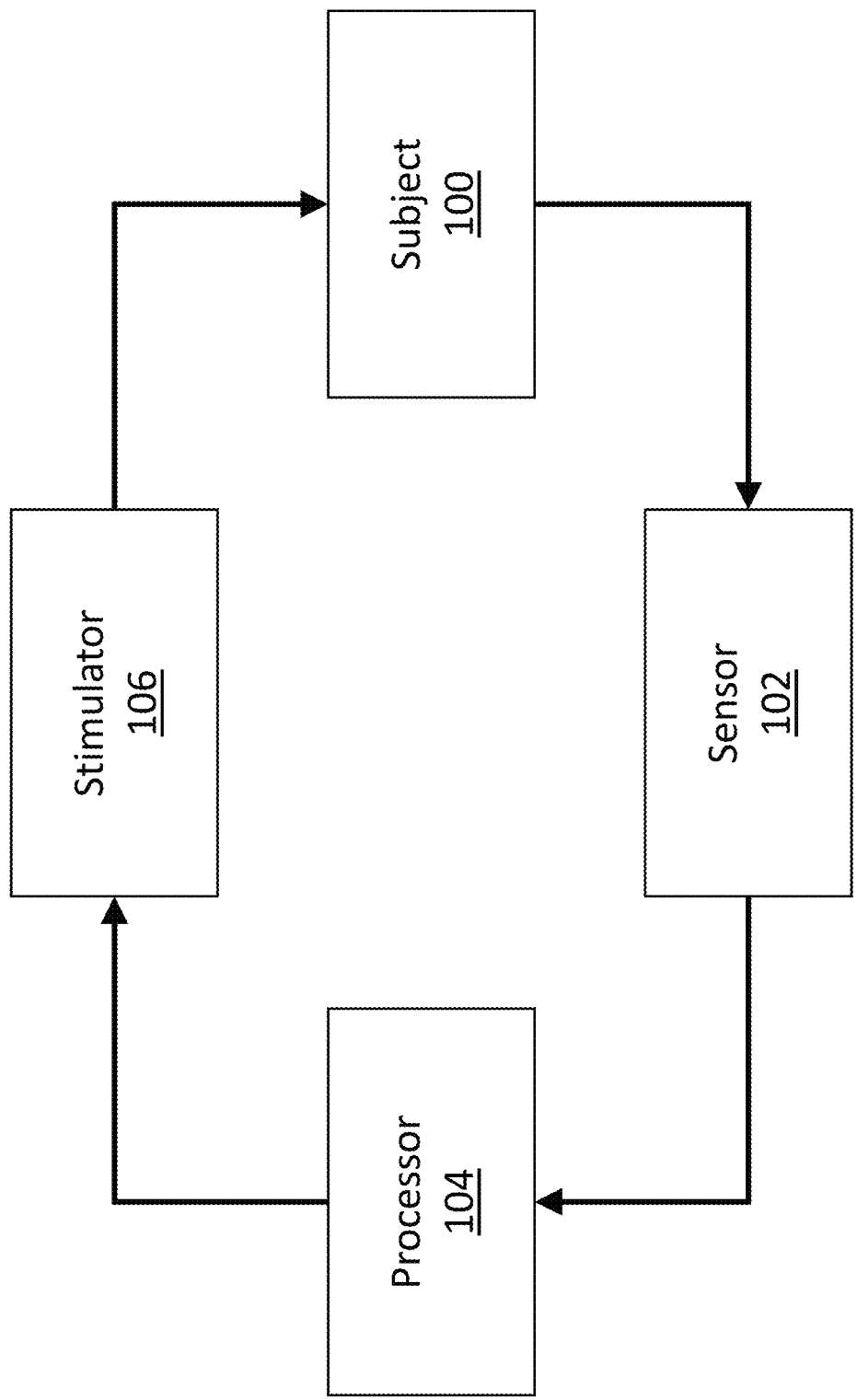
FIG. 1 illustrates closed-loop stimulation.

Closed-loop stimulation refers to controlled stimulation in response to a detected physiological state or parameter. An example closed-loop stimulation system is illustrated in FIG. 1. According to such a system (and corresponding method), a physiological parameter (e.g., ECG, EEG, blood pressure, heart rate, blood oxygen saturation, and the like) is measured from a subject 100 by at least one sensor 102. The measured parameters are analyzed by at least one processor 104 (e.g., implementing a machine learning system), such as those associated with one or more computer system. Based on a result of the analysis, the processor 104 causes stimulation by a stimulator 106 to be activated and/or stopped. The results of the analysis may indicate, for example, that one of the measured parameters reaches a threshold level, or that the parameters (individually or collectively) indicate a particular condition.

As it relates to myocardial ischemia, the closed-loop stimulation of the present disclosure monitors a cardiovascular state of a subject before, during, and/or after a myocardial ischemia event. More particularly, cardiovascular data including a lead II electrocardiogram (ECG), intraarterial blood pressure, and/or a photoplethysmogram of the subject are monitored. Non-cardiovascular data, such as a galvanic skin response and/or electroencephalograph, may also be monitored to assess the cardiovascular state. Features of the monitored data can be extracted from the monitored data and analyzed for patterns corresponding to myocardial ischemia. A non-limiting list of features that may be extracted from an ECG, blood pressure, and photoplethysmogram measurements for further analysis includes any one or combination of: 1) heart rate, 2) QRS interval (ms), 3) RT interval (ms), 4) ST interval (ms), 5) Q wave level (mV), 6) R wave level, 7) ST segment level (mV), 8) ST segment slope, 9) diastolic pressure, 10) systolic pressure, 11) mean arterial pressure, 12) pulse pressure, and/or 13) breath rate.

Such parameters, and the analyses thereof, can be helpful in identifying several cardiovascular changes that occur during myocardial ischemia, and thus in determining the onset, existence of, or a prior ischemic event. For example, the lead II ECG shows a depression (of about half) of the S-T epoch during ischemia. Other example biomarkers that can indicate myocardial ischemia include but are not limited to: an elevation of the S-T segment indicating transmural myocardial ischemia (similar to a myocardial infarction), prolonged durations of heart rate and blood pressure increases, and ECG interval variability indicating electrical instability of the myocardium (e.g., increases in Q-T interval length and variability).

Figure 2:
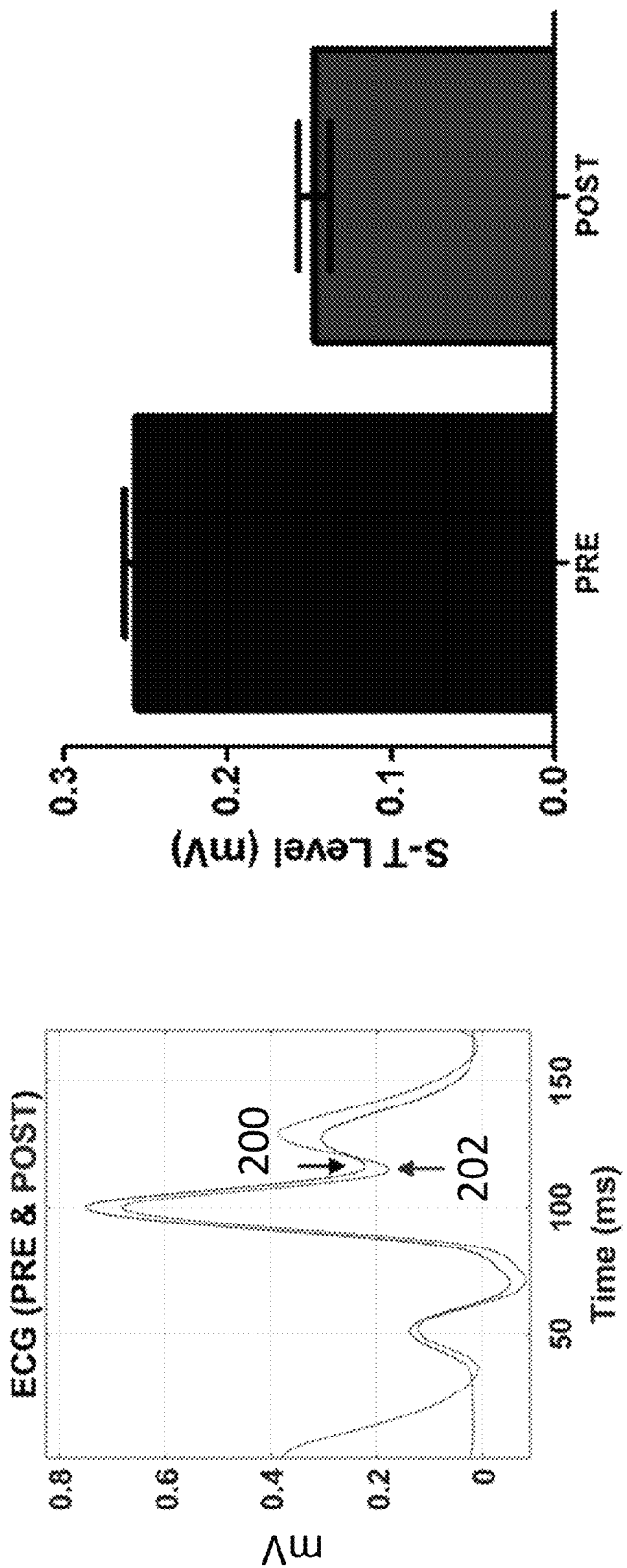
FIG. 2 illustrates an exemplary S-T epoch depression during a myocardial ischemia event.

An exemplary S-T epoch depression is illustrated in FIG. 2. Therein, the lead II ECG signal is illustrated during a pre-ischemic period 200 and a post-ischemic period 202 (the S-T epoch being identified at the arrows in the figure) during a single trial. The quantified level difference of the S-T epoch across multiple trials is also shown in FIG. 2, with the S-T level dropping from about 0.25 mV to about 0.15 mV. This change is caused by the decrease in myocardial oxygen, which significantly depolarizes the interior wall of the left ventricle. It is also noted that the S-T depression may be visible on a composite ECG signal, and is not limited to identification via a lead II signal. Other correlates of ischemia include at least an increased heart rate, a decrease in the J point of the ECG waveform, and an increase in the product of heart rate and blood pressure.

Analysis of the extracted features can be performed by machine learning systems (e.g., implemented by the at least one processor 104 discussed above). For example, such systems can include non-linear support vector machines (SVMs) and long short-term memory (LSTM) deep learning networks. Preliminary experiments indicate that LSTM networks have ~90% overall accuracy and SVMs have about ~75% accuracy in detecting myocardial ischemia from the above-noted extracted features. LSTMs can detect changes in a time series via a 'learned memory'. In other words, LSTMs are able to access 'the history of changes' several time steps into the past for event prediction, unlike other machines that make instantaneous predictions independent of historic data. Because LSTMs are sensitive to context within a time series, they are capable of not only detecting myocardial ischemia, but also detecting certain time points during myocardial ischemia development (e.g., 'early' ischemia vs. 'late' ischemia). This ability to leverage a memory may further optimize performance and eventual therapy.

Figure 3:
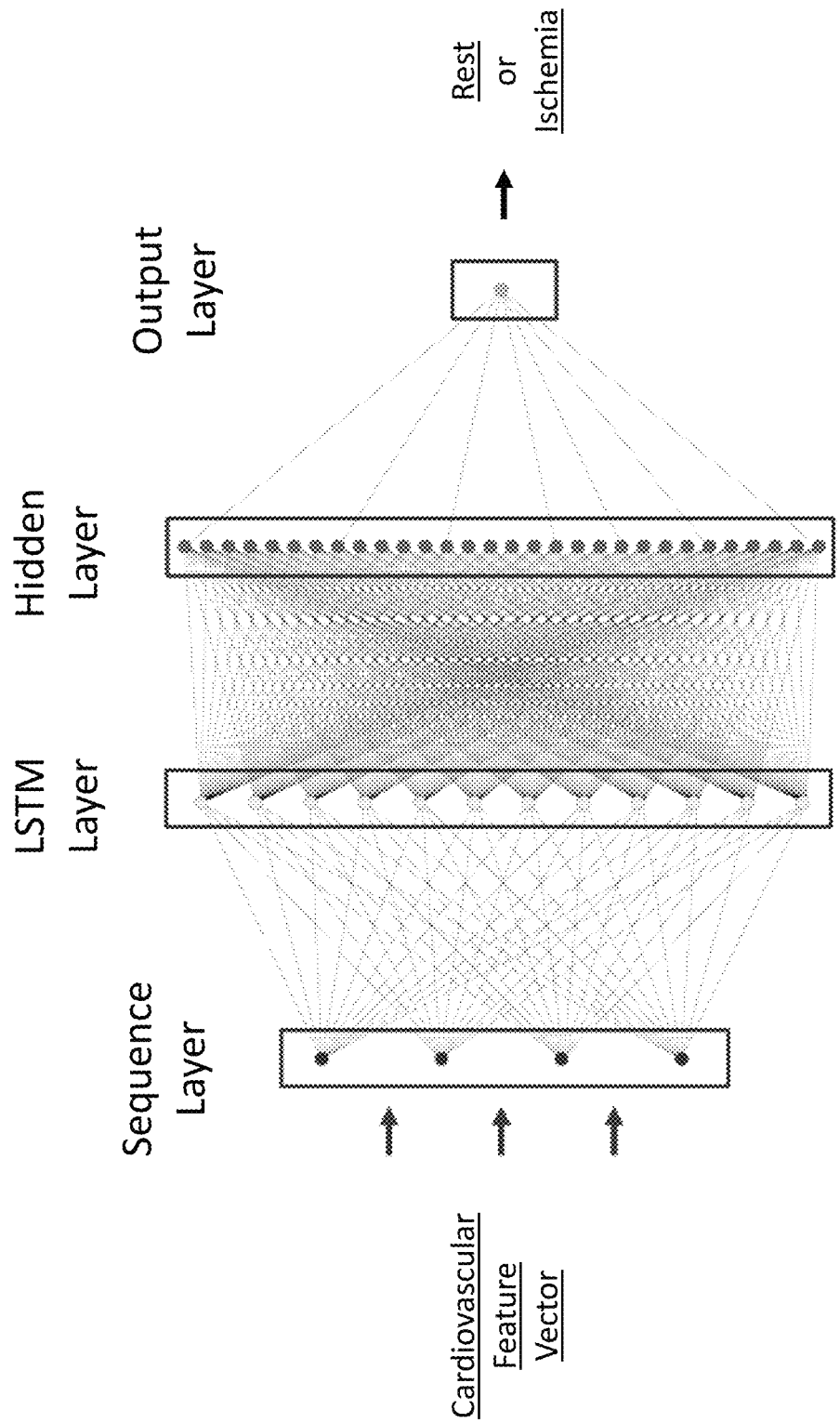
FIG. 3 illustrates an example machine learning system architecture incorporating a long short-term memory (LSTM) layer.

An example machine learning system architecture incorporating an LSTM layer is illustrated in FIG. 3. Therein, any one or combination of the above-noted thirteen extracted features (and/or other relevant features) are input (e.g., as a cardiovascular feature vector) into a sequence layer of thirteen units (or other number of units corresponding to the number of extracted features input thereto). The sequence layer is fully connected to an LSTM layer of, for example, 100 units, and is configured to sequence the inputted features for the LSTM layer. As noted above, the LSTM layer is configured to recall and learn long-term dependencies in the sequence. The LSTM layer is fully connected to a hidden layer of, for example, 250 units. The hidden layer is configured to learn the relationships between the outputs of the LSTM layer and a physiological state (e.g., a 'rest' or 'ischemia' state). The hidden layer is about 25% connected to an output layer, which has two units corresponding to each possible output state (e.g., rest or ischemia) (or other number of units corresponding to another number of possible output states). In short, the LSTM machine learning system identifies whether the input features correspond to a rest or ischemia state, and thus can identify the physiological state of a subject from which the features were extracted.

The machine learning system can be trained with data segments that are approximately 210 seconds long. The first approximately 90 seconds are during 'rest' states, which represents a baseline physiological state when there is no myocardial ischemia state. For laboratory simulations, the rest state corresponds to a period prior to injection of ischemia inducing drugs. The remaining data segment (approximately 120 seconds) are during an ischemic state. For laboratory simulations, the ischemic state corresponds to a period following injection of the ischemia inducing drugs. Myocardial ischemia develops progressively (in simulation, once the injection starts), and generally reaches a maximum level of severity around 40-50 seconds after onset.

Figure 4:
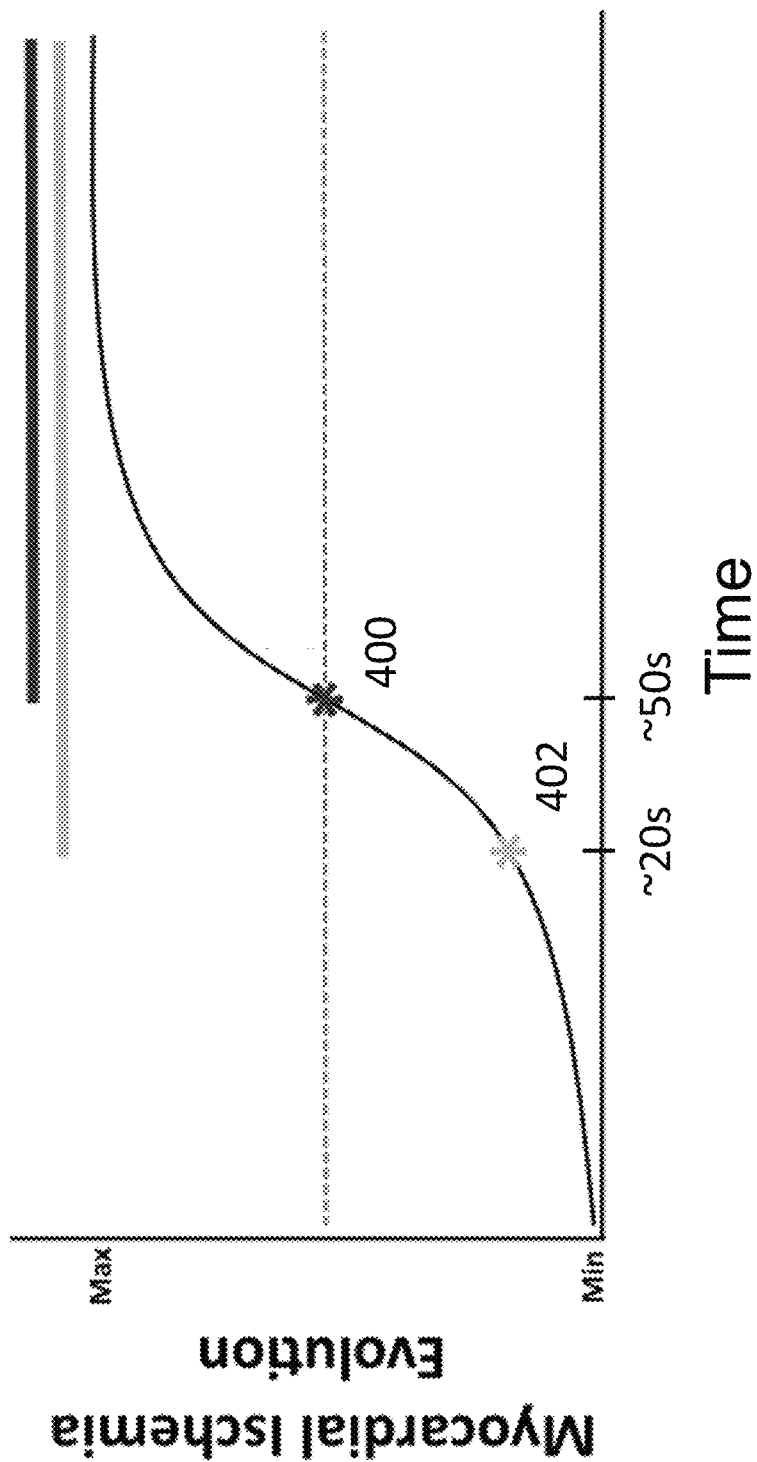
FIG. 4 illustrates prediction timings of 'Early' and 'Late' LSTM machine learning systems.

FIG. 4 illustrates two machine learning systems trained to detect myocardial ischemia at different times. A first machine learning system (hereinafter 'Late LSTM') 400 is trained with data such that the system is configured to identify ischemia only when the ischemia reached statistically significant threshold evolution level (e.g., when an S-T depression occurs). The threshold level is illustrated by the dashed line in FIG. 4. A second machine learning system (hereinafter 'Early LSTM') 402 is trained with data such that the system is configured to identify ischemia closer to onset, about 45 seconds before the statistically significant threshold is reached. In one example of the Early LSTM system, ischemia is detected at about 20 seconds into ischemia development, prior to the ischemia being fully developed. In contrast, an example of the Late LSTM system (trained to recognized ischemic events at statistically significant S-T depressions) does not detect ischemia until later at about 50 seconds into development. This time corresponds to when ischemia has essentially fully developed and has reached (or nearly reached) its maximum level and severity.

Such trained machine learning systems can be incorporated into a closed-loop Vagus nerve stimulation system and method, for example as part of one or more processors 104 described with respect to FIG. 1. As discussed above, such a closed-loop stimulation system and method may include measuring, with appropriate sensors 102, physiological information from a subject 100. These sensors may comprise, for example, a lead II electrocardiogram (ECG), intraarterial blood pressure sensor, and/or a photoplethysmogram. From the measured data, each of the above features may be extracted and input into the trained machine learning system. Finally, vagal nerve stimulation can be activated via a vagal nerve stimulation device 106 when the trained machine learning outputs, based on the input physiological features, an ischemia state. In one example, the vagal nerve stimulation device 106 comprises electrodes (e.g., cuff electrodes) configured to stimulate the Vagus nerve, a controller/processor, and a generator. The controller/processor of the stimulation device 106 may control a voltage or current output of the generator to the electrode to control stimulation of the Vagus nerve in accordance with an output of the machine learning system and processor 104. In one example, VNS may be applied to the left cervical Vagus nerve via a bipolar stimulating cuff interface/electrode, and/or applied stimulation may be according to a biphasic square wave morphology at 2.5 mA and 30 Hz, with a 0.3 millisecond pulse width. More generally, the stimulation may be at 0.5-3 mA and 1-60 Hz, with a 100-400 µs pulse width. However, the present disclosure is not limited to such stimulation protocols. It is also noted that the above hardware may be integrated in any manner in some embodiments. For example, various computers and processors 104, the machine learning system, and the controller/processor of the stimulation device may be integrated/embodied as a single computer or integrated circuit or embodied as separate elements.

Figure 5:
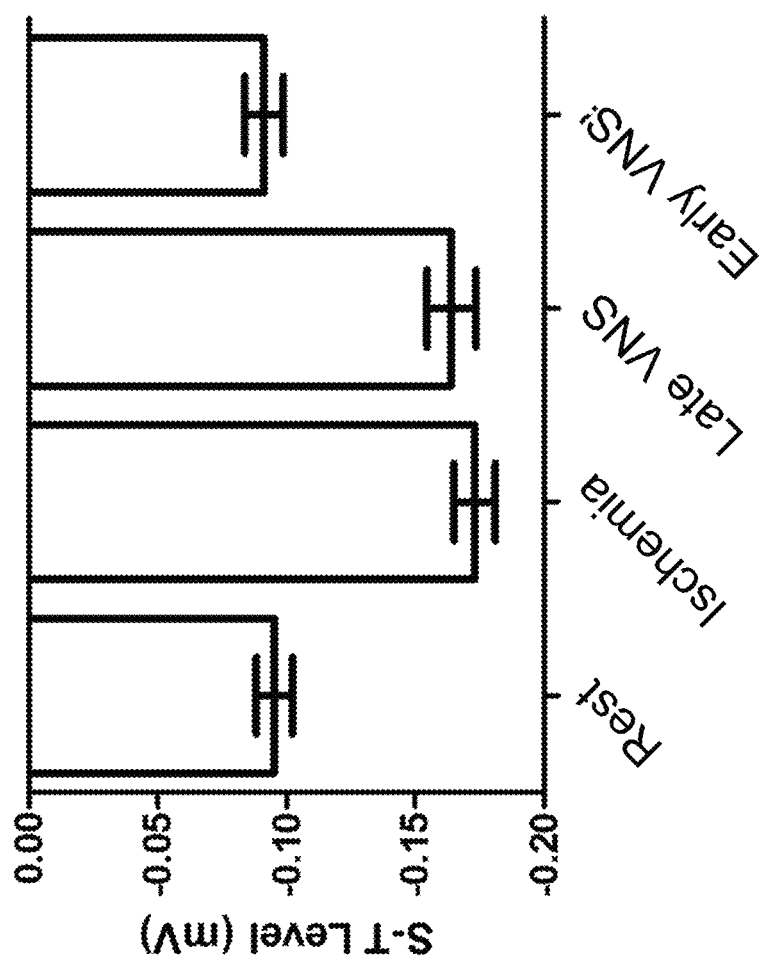
FIG. 5 illustrates the level of the S-T epoch during rest and ischemia conditions, as well as the levels following VNS triggered by each of the Early and Late LSTM systems.
Figure 6:
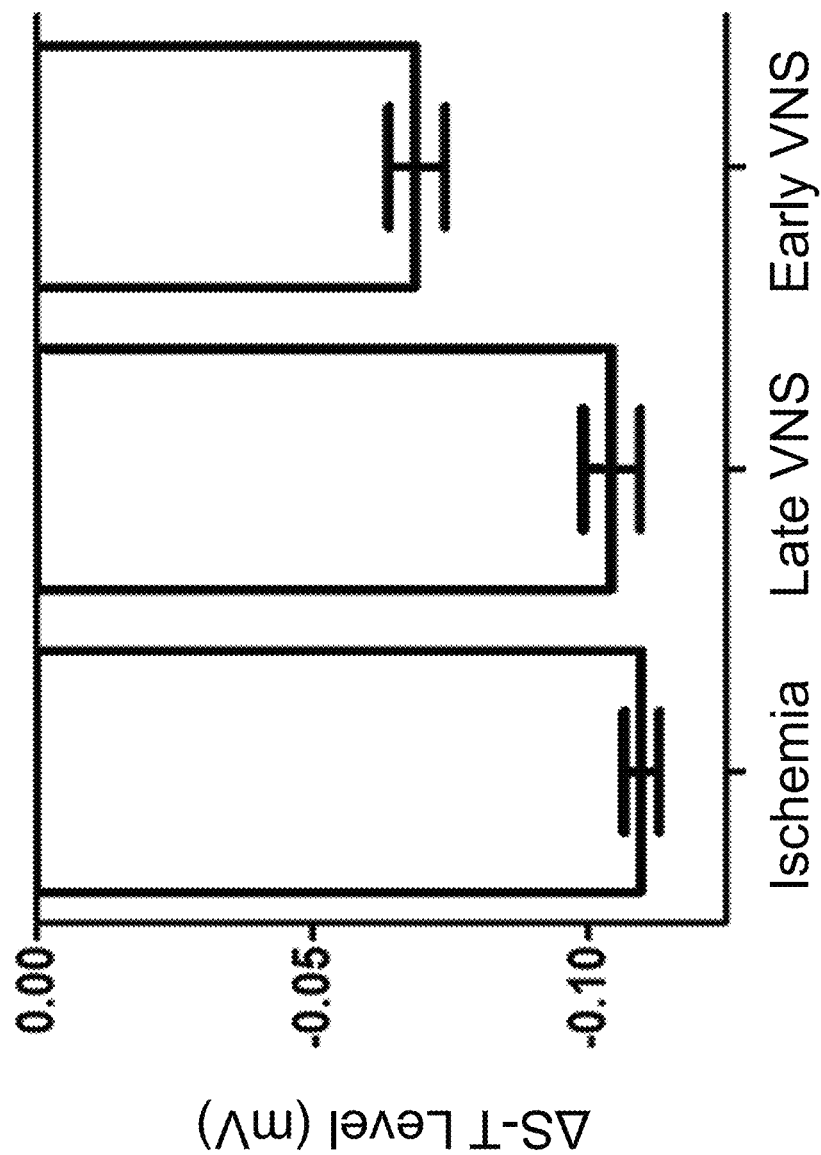
FIG. 6 illustrates the change in S-T level relative to a resting state during ischemia, and following VNS triggered by each of the Early and Late LSTM systems.

As noted above, the timing of VNS can have an impact on the success of VNS in reversing or mitigating an ischemia event. And as part of a closed-loop stimulation system, the timing of VNS is controlled by the identification of an ischemia event (e.g., as output by an LSTM machine learning system). Accordingly, an LSTM machine learning system should be trained to identify ischemia within the therapeutic window in which VNS is successful. The relative effectiveness of the above-described Early and Late LSTM systems is illustrated in FIGS. 5 and 6. More particularly, FIG. 5 illustrates the level of the S-T epoch during rest and ischemia conditions, as well as the levels following VNS triggered by each of the Early and Late LSTM systems. As seen therein, VNS triggered by the Late LSTM system had little or no reversal effects on the S-T level (and thus the ischemia). However, VNS triggered by the Early LSTM system significantly reduced the S-T level effect of ischemia to the resting level. This effect is further seen in FIG. 6, which illustrates the change in S-T level relative to a resting state during ischemia, and following VNS triggered by each of the Early and Late LSTM systems. As can be seen again, VNS results in little or no change to the S-T level depression when triggered by the Late LSTM system, while the change in S-T level is reduced by half when VNS is triggered by an Early LSTM system. Although not shown, it is also noted that additional significant reversal or mitigation effects of ischemia by VNS are seen in decreased heart rate, decreased J point, and decreased product of heart rate and blood pressure.

In view of the above, VNS is timely and can thus successfully reverse (or at least significantly mitigate) myocardial ischemia when applied within a therapeutic window, but can be ineffective when applied outside of that window. As indicated by FIG. 4, this window is between 0 and 50 seconds of the onset of ischemia. Put another way, and considering the details of the two machine learning systems discussed above, closed-loop VNS stimulation is applied within the therapeutic window when triggered by the output of a machine learning system trained to identify myocardial ischemia with data identifying the myocardial ischemia prior to the myocardial ischemia reaching a statistically significant evolution level.

What we claim is:
1. A stimulation system comprising:
at least one sensor configured to monitor physiological data of a subject;
a trained machine learning system configured to identify a myocardial ischemia state of the subject based on the monitored physiological data; and
an electrode configured to stimulate the Vagus nerve of the subject when the machine learning system identifies the myocardial ischemia state of the subject, wherein:
the machine learning system is trained with segments of physiological data, the segments including a rest state and a myocardial ischemia state, and
the myocardial ischemia state is identified in the training segments prior to the myocardial ischemia reaching a statistically significant evolution level.

2. The stimulation system of claim 1, wherein the physiological data includes a lead II electrocardiogram (ECG), intraarterial blood pressure, and/or a photoplethysmogram.

3. The stimulation system of claim 1, wherein a heart rate, QRS interval, RT interval, ST interval, Q wave level, ST segment level, ST segment slope, diastolic pressure, systolic pressure, mean arterial pressure, pulse pressure, and/or breath rate are extracted from the physiological data and input to the trained machine learning system.

4. The stimulation system of claim 1, wherein the segments of physiological data include a heart rate, QRS interval, RT interval, ST interval, Q wave level, ST segment level, ST segment slope, diastolic pressure, systolic pressure, mean arterial pressure, pulse pressure, and/or breath rate information.

5. The stimulation system of claim 1, wherein the trained machine learning system comprises a long short-term memory deep learning layer.

6. The stimulation system of claim 1, wherein the electrode is configured to stimulate the Vagus nerve with a biphasic square wave morphology at 0.5-3 mA and 1-60 Hz, with a 100-400 µs pulse width.

7. The stimulation system of claim 1, wherein the electrode is configured to stimulate the Vagus nerve with a biphasic square wave morphology at 2.5 mA and 30 Hz, with a 0.3 millisecond pulse width.

8. A stimulation method comprising:
monitoring physiological data of a subject;
identifying, with a trained machine learning system, a myocardial ischemia state of the subject based on the monitored physiological data; and
stimulating the Vagus nerve of the subject when the machine learning system identifies the myocardial ischemia state of the subject, wherein:
the machine learning system is trained with segments of physiological data, the segments including a rest state and a myocardial ischemia state, and
the myocardial ischemia state is identified in the segments prior to the myocardial ischemia reaching a statistically significant evolution level.

9. The stimulation method of claim 8, wherein the physiological data includes a lead II electrocardiogram (ECG), intraarterial blood pressure, and/or a photoplethysmogram.

10. The stimulation method of claim 8, further comprising:
extracting a heart rate, QRS interval, RT interval, ST interval, Q wave level, ST segment level, ST segment slope, diastolic pressure, systolic pressure, mean arterial pressure, pulse pressure, and/or breath rate from the physiological data; and
inputting the extracted information to the trained machine learning system.

11. The stimulation method of claim 8, wherein the segments of physiological data include a heart rate, QRS interval, RT interval, ST interval, Q wave level, ST segment level, ST segment slope, diastolic pressure, systolic pressure, mean arterial pressure, pulse pressure, and/or breath rate information.

12. The stimulation method of claim 8, wherein the trained machine learning system comprises a long short-term memory deep learning layer.

13. The stimulation method of claim 8, wherein the Vagus nerve is stimulated with a biphasic square wave morphology at 0.5-3 mA and 1-60 Hz, with a 100-400 µs pulse width.

14. The stimulation method of claim 8, wherein the Vagus nerve is stimulated with a biphasic square wave morphology at 2.5 mA and 30 Hz, with a 0.3 millisecond pulse width.

* * * * *